(12) United States Patent
Brauer et al.

(10) Patent No.: US 10,600,175 B2
(45) Date of Patent: Mar. 24, 2020

(54) DYNAMIC CARE AREAS FOR DEFECT DETECTION

(71) Applicant: KLA-Tencor Corporation, Milpitas, CA (US)

(72) Inventors: Bjorn Brauer, Beaverton, OR (US); Benjamin Murray, Portland, OR (US); Shishir Suman, Bihar (IN); Lisheng Gao, Saratoga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 74 days.

(21) Appl. No.: 15/858,264

(22) Filed: Dec. 29, 2017

(65) Prior Publication Data
US 2018/0276808 A1 Sep. 27, 2018

Related U.S. Application Data

(60) Provisional application No. 62/476,060, filed on Mar. 24, 2017, provisional application No. 62/478,425, (Continued)

(51) Int. Cl.
| | | |
|---|---|---|
| G06T 7/00 | (2017.01) | |
| G01N 21/95 | (2006.01) | |
| G01N 21/88 | (2006.01) | |
| G01N 21/956 | (2006.01) | |
| G06T 7/73 | (2017.01) | |
| G06F 17/50 | (2006.01) | |

(52) U.S. Cl.
CPC ....... *G06T 7/0006* (2013.01); *G01N 21/8851* (2013.01); *G01N 21/9501* (2013.01); *G01N 21/95607* (2013.01); *G06F 17/5081* (2013.01); *G06T 7/001* (2013.01); *G06T 7/74* (2017.01); *G01N 2021/8861* (2013.01); *G06T 2207/30148* (2013.01)

(58) Field of Classification Search
CPC ......... G06T 7/0006; G06T 7/74; G06T 7/001; G06F 17/5081; G01N 21/9501; G01N 21/8851; G01N 21/95607; G01N 2021/8861
USPC ........................................................ 716/52
See application file for complete search history.

(56) References Cited

U.S. PATENT DOCUMENTS

| | | | | |
|---|---|---|---|---|
| 8,781,781 B2* | 7/2014 | Kulkami | ............ | G05B 23/0297 702/108 |
| 9,075,026 B2* | 7/2015 | Urano | ................ | G01N 21/9501 |

(Continued)

FOREIGN PATENT DOCUMENTS

WO 2009015084 A1 1/2009

OTHER PUBLICATIONS

ISA/KR, International Search Report for PCT/US2018/023671 dated Jul. 9, 2018.

*Primary Examiner* — Stacy Whitmore
(74) *Attorney, Agent, or Firm* — Hodgson Russ LLP (57) ABSTRACT

Systems and methods of a two-pass inspection methodology that dynamically creates micro care areas for inspection of repeater defects. Micro care areas can be formed around each location of a repeater defect. After inspection, additional repeater defects in the micro care areas can be identified. Attributes of the repeater defects can be compared and any repeater defects with attributes that deviate from an expected group attribute distribution can be classified as nuisance.

17 Claims, 7 Drawing Sheets

Related U.S. Application Data filed on Mar. 29, 2017, provisional application No. 62/515,449, filed on Jun. 5, 2017.

(56) References Cited

U.S. PATENT DOCUMENTS

| | | |
|---|---|---|
| 2006/0078188 A1 | 4/2006 | Kurihara et al. |
| 2006/0115143 A1 | 6/2006 | Auerbach |
| 2011/0211060 A1 | 9/2011 | Funakoshi et al. |
| 2014/0157213 A1* | 6/2014 | Hsieh .................. G03F 7/705 716/52 |
| 2015/0178907 A1* | 6/2015 | Zhang .................. G06T 7/001 382/149 |
| 2015/0254394 A1* | 9/2015 | Hu .................. G01N 21/9501 716/52 |
| 2016/0071256 A1 | 3/2016 | Wu et al. |
| 2016/0223470 A1* | 8/2016 | O'Dell ............... G01N 21/9501 |
| 2017/0091925 A1* | 3/2017 | Wu ..................... G06T 7/001 |

* cited by examiner

DYNAMIC CARE AREAS FOR DEFECT DETECTION

CROSS-REFERENCE TO RELATED APPLICATIONS

This application claims priority to the provisional patent application filed Mar. 24, 2017 and assigned U.S. App. No. 62/476,060, the provisional patent application filed Mar. 29, 2017 and assigned U.S. App. No. 62/478,425, and the provisional patent application filed Jun. 5, 2017 and assigned U.S. App. No. 62/515,449, the disclosures of which are hereby incorporated by reference.

FIELD OF THE DISCLOSURE

This disclosure relates to defect detection.

BACKGROUND OF THE DISCLOSURE

Evolution of the semiconductor manufacturing industry is placing ever greater demands on yield management and, in particular, on metrology and inspection systems. Critical dimensions are shrinking while wafer size is increasing. Economics is driving the industry to decrease the time for achieving high-yield, high-value production. Thus, minimizing the total time from detecting a yield problem to fixing it determines the return-on-investment for the semiconductor manufacturer.

Repeater defects are a concern to semiconductor manufacturers. Repeater defects are defects that appear on a wafer with some regular periodicity and that show some fixed relationship to the die layout on a reticle or stepping pattern on a wafer. Reticle defects are a common cause of repeater defects. Reticle defects that can cause repeater defects include, for example, extra chrome pattern on a mask plate, missing chrome on a mask plate, particulates on the mask plate or on the reticle, and damage to the pellicle.

For example, a print check application can include detection of reticle defects. These reticle defects occur on multiple reticles across the wafer and can be seen as either soft repeaters (less than 50% occurrence) or hard repeaters (more than 50% occurrence). A print check application can identify all unique repeater candidates and identify all locations where the repeater defect is printed.

Previously, reticle repeater inspection was performed by die-to-die or reticle-to-reticle inspection where each die or reticle is compared with surrounding dies or reticles. Repeater identification was performed after the inspection, such as during post processing. This technique has reduced sensitivity because of higher surrounding noise. These kinds of inspections also generate a high count of events during the scan. Thus, repeater events with signal may fail to be detected because of tool capabilities to handle high defect counts.

Broad band plasma (BBP) tools may use die-to-die inspection for repeater identification. However, this technique has lower sensitivity due to higher surrounding noise. Furthermore, the BBP tools may be lack the capability to handle a necessary number of defects before post-processing, such as greater than 1.7 million defects.

Reticle repeater inspection also was performed by robust average algorithms such as Repeater-in Array (RIA) or Standard Reference Die 1 (SRD 1) based on a robust average image. Such algorithms remove an outlier event for every pixel. This reduces random events during detection. This technique may not accurately identify printability variations or perform a robust recipe setup. In such algorithms, after a repeater is detected, the locations are copied to all the inspected dies or reticles on the row. However, separating the defect from a printed location to a not printed location can be challenging. The only available attribute to do so (e.g., repeater signal) is not always effective. Such attributes may be ineffective when analyzed across different repeaters.

BBP tools also can be used with robust average algorithms to detect repeaters. After a robust average algorithm detects a repeater, the location is copied to all the inspected reticles on the die row. Using a robust average instead can suffer from recipe setup and printability variation challenges. Separating the defect from a printed location to a not printed location can be challenging because it uses the repeater signal.

Furthermore, high nuisance rates are a common problem during these inspections. This can prevent the BBP tool from running hot enough to find small defects (e.g., into the noise floor). Previous techniques calculated attributes of individual defects, but separating defects of interest (DOI) and nuisance defects is often difficult, which can result in a high nuisance rate.

Therefore, a new technique to detect repeater defects is needed.

BRIEF SUMMARY OF THE DISCLOSURE

In a first instance, a method is provided. The method comprises determining locations, using a processor, of repeater defects on a wafer. Using the processor, a micro care area is created around each of the locations. The micro care areas on the wafer are inspected using a wafer inspection tool. Additional repeater defects are identified in the micro care areas. Using the processor, at least one attribute of the repeater defects and the additional repeater defects is compared. Using the processor, any of the repeater defects and the additional repeater defects with the attribute (e.g., an instance of the attribute) that deviates from an expected group attribute distribution are classified as nuisance.

The group attribute distribution may be based one or more of: all identified repeater defects on the wafer; all repeater defects of a same defect type; all repeater defects with a same design structure on the wafer; all repeater defects with a same die coordinate; all repeater defects with a same reticle coordinate; all repeater defects with a same background structure; or all repeater defects with a same wafer-to-wafer coordinate across multiple wafers.

The attribute can include polarity. The attribute also can include at least one of shape of a point spread function, contour of a point spread function, size, brightness, or feature vectors.

The determining may be for an entirety of a surface of the wafer or may be for only a die row on the wafer.

The method can further include generating, using the processor, locations on the wafer to skip during a subsequent inspection due to presence of the nuisance.

Determining the locations can include using repeater in array or standard reference die for logic areas. Determining the locations also can include a die-to-die inspection.

In a second instance, a system is provided. The system includes a processor and an electronic data storage unit in electronic communication with the processor. The processor is in electronic communication with a wafer inspection tool. The processor is configured to execute instructions that: determine locations of repeater defects on a wafer; create a micro care area around each of the locations; identify additional repeater defects in the micro care areas based on an additional inspection of the micro care areas; compare at least one attribute of the repeater defects and the additional repeater defects; and classify any of the repeater defects and the additional repeater defects with the attribute (e.g., an instance of the attribute) that deviates from an expected group attribute distribution as nuisance.

The group attribute distribution may be based on one or more of: all identified repeater defects on the wafer; all repeater defects of a same defect type; all repeater defects with a same design structure on the wafer; all repeater defects with a same die coordinate; all repeater defects with a same reticle coordinate; all repeater defects with a same background structure; or all repeater defects with a same wafer-to-wafer coordinate across multiple wafers.

The attribute can include polarity. The attribute also can include at least one of shape of a point spread function, contour of a point spread function, size, brightness, or feature vectors.

The processor may be further configured to execute instructions that generate locations on the wafer to skip during a subsequent inspection due to presence of the nuisance.

The processor may be part of the wafer inspection tool.

In a third instance, a method is provided. The method comprises receiving, at a processor, a plurality of repeater defects. Using the processor, at least one attribute of the repeater defects is compared. The attribute includes at least polarity of the repeater defects. Using the processor, any of the repeater defects with attributes (e.g., an instance of the attribute) that deviate from an expected group attribute distribution are separated as nuisance.

The group attribute distribution may be based on one or more of: all identified repeater defects on the wafer; all repeater defects of a same defect type; all repeater defects with a same design structure on the wafer; all repeater defects with a same die coordinate; all repeater defects with a same reticle coordinate; all repeater defects with a same background structure; or all repeater defects with a same wafer-to-wafer coordinate across multiple wafers.

The attribute can further include at least one of shape of a point spread function, contour of a point spread function, size, brightness, or feature vectors.

The method can further include generating, using the processor, locations on a wafer to skip during a subsequent inspection due to presence of the nuisance.

In a fourth instance, a method for filtering nuisance is provided. The method comprises imaging a first die and a second die using a reticle at two different positions on a first wafer and two different positions on a second wafer. A difference image of the second wafer in a second wafer step is calculated by: calculating, using a processor, a difference image of the first die and the second die at a second position on the second wafer; calculating, using the processor, a difference image of the first die at the second position on the first wafer and the second die at a first position on the second wafer; and calculating, using the processor, the difference image of the second wafer using the two difference images of the second wafer step. Using the processor, existence of a defect of interest in the wafer difference image of the second wafer is determined.

The method can further comprise retrieving images from the storage medium. The images are at a same location on the first wafer as the first die and the second die on the second wafer. Using the processor, presence of the defect of interest in the images from the storage medium is evaluated. Using the processor, nuisance is filtered from the second wafer difference image.

The method can further comprise calculating a difference image of the first wafer in a first wafer step. Calculating a difference image of the first wafer in a first wafer step includes calculating, using the processor, a difference image of the first die and the second die at a second position on the first wafer. Using the processor, a difference image of the first die at the second position on the first wafer and the second die at a first position on the first wafer is calculated. Using the processor, the wafer difference image of the first wafer using the two difference images of the first wafer step is calculated. Using the processor, systematic defects in the difference image of the first wafer are found using coordinate-based defect source analysis. Using the processor, the systematic defects in the difference image of the first wafer are subtracted from the difference image of the second wafer. Determining existence of the defect of interest in the difference image of the second wafer is after the subtracting.

The method can further comprise calculating a difference image of the first wafer in a first wafer step. Calculating a difference image of the first wafer in a first wafer step includes calculating, using the processor, a difference image of the first die and the second die at a second position on the first wafer. Using the processor, a difference image of the first die at the second position on the first wafer and the second die at a first position on the first wafer is calculated. Using the processor, the difference image of the first wafer using the two difference images of the first wafer step is calculated. Using the processor, the difference image of the second wafer is subtracted from the difference image of the first wafer. Determining existence of the defect of interest in the difference image of the second wafer is after the subtracting.

The embodiments of the method of the fourth instance may be used with the methods of the first instance or third instance or may be performed by the system of the second instance.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments disclosed herein can use a two-pass inspection methodology that includes dynamically creating micro care areas, which can be used as an inspection method for robust monitoring of reticle repeaters. The micro care areas can provide enhanced capture of reticle repeaters for print check applications. Use of a database of dynamic micro care areas can provide a more robust inspection monitoring flow. Likelihood of finding soft repeaters may be improved due to enhanced sensitivity.

The embodiments disclosed herein can be applied to improve sensitivity of BBP tool inspection of reticle repeaters, particularly in instances where the BBP tool faces a lower capture than the ground truth.

Figure 1:
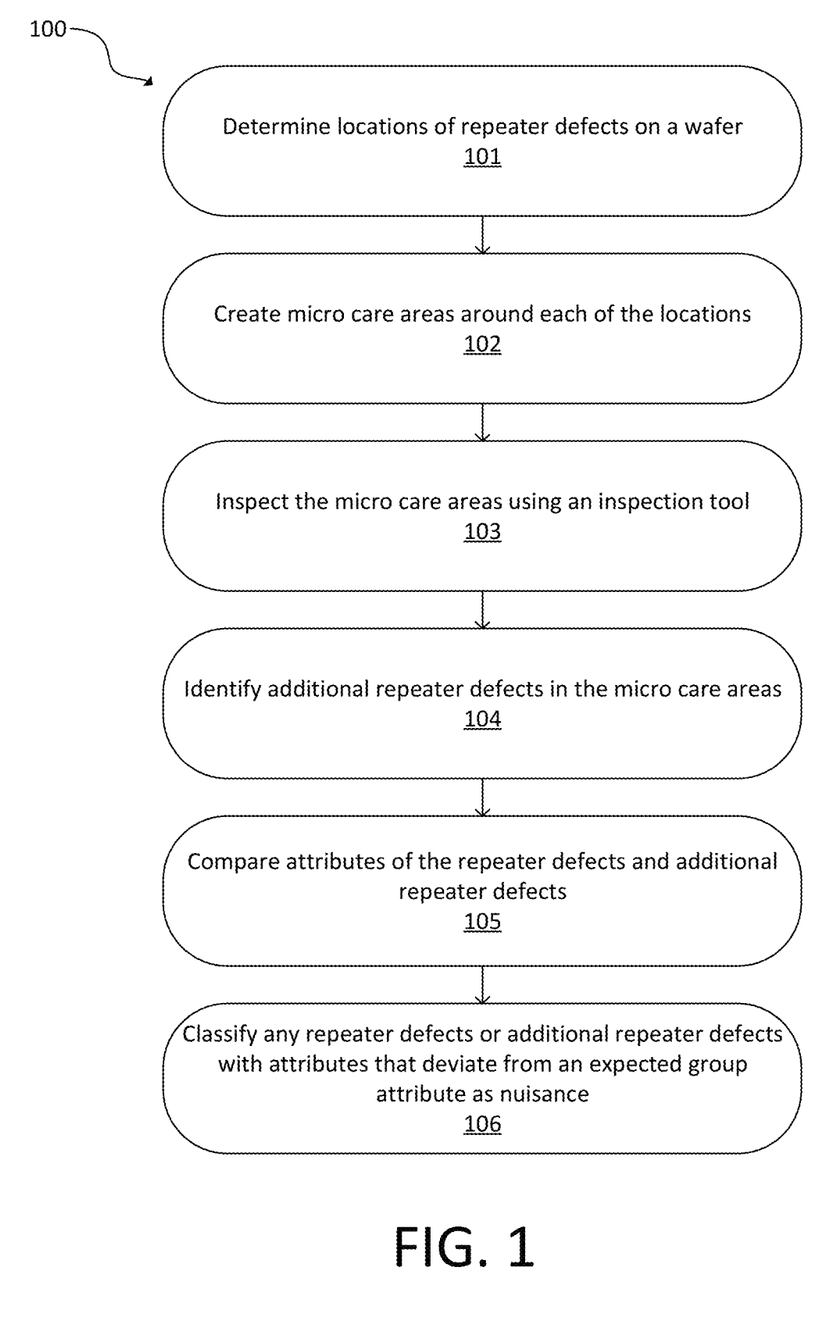
FIG. 1 is a flowchart of an embodiment of repeater defect detection in accordance with the present disclosure.

FIG. 1 illustrates a method 100 that includes inspection with dynamic micro care areas. Locations of repeater defects on a wafer are determined at 101. This can be for an entirety of a surface of the wafer or only part of a surface of the wafer, such as only a die row on the wafer. In an instance, the repeater defect locations may be found with robust average algorithms such as repeater in array (RIA) or standard reference die (SRD) for logic areas or die-to-die inspections. Robust averaging is an algorithm which calculates the average of a certain number of reference frames and removes outliers such as single pixel noise. RIA averages many cells within an array and compares them to the candidate image. The robust average algorithms may allow the scan to run hotter than die-to-die inspections, but die-to-die inspections can be used. SRD calculates a reference image on a golden (e.g., a reference or clean) die on a reference wafer. This then can be compared to an image on the inspection wafer, and the difference image will be calculated.

Micro care areas are created around each of the locations at 102. The care areas may be created around defects with the pixel of the highest difference grey level in the center of the micro care area.

For example, micro care areas may be formed around each of the locations with a unique repeater defect. The micro care areas can provide high sensitivity for any repeater. This increases the likelihood of capturing higher numbers of repeater events compared to other methodologies.

The micro care areas may have dimensions from one pixel to approximately ten pixels. So the micro care areas may be from one pixel square to a ten by ten pixel square, including all ranges and integer pixel values therebetween.

Additionally, the micro care areas can be formed in locations on the wafer where no repeater defects were detected, but where repeater defects are expected based on the locations of the repeater defects.

The micro care areas can be dynamic. By dynamic, the micro care areas can have different sizes. For example, micro care areas may be larger to ensure defects are not missed (e.g., 7×7 pixels) for areas on the die or wafer where the alignment accuracy is lower than other areas. At locations where the alignment accuracy of the care areas with respect to the wafer images is better, then a smaller (e.g., 3×3 pixel) micro care area may be used.

At 103, the micro care areas on the wafer are inspected using an inspection tool, such as a scanning electron microscope (SEM) or a BBP tool.

Additional repeater defects are identified in the micro care areas at 104. The inspection can be performed with higher sensitivity because there are a small number of micro care areas to inspect relative to an entire wafer surface. In an instance, only the micro care areas are inspected on the wafer. For example, a reticle mask which has a particle on it may print fifty times on a wafer. Since fifty locations on the wafer are inspected with this care area, this particle defect can be detected up to fifty times. Thus, all those fifty defects belong to the same care area.

Attributes of the repeater defects and the additional repeater defects (if any) are compared at 105. Any of the repeater defects and the additional repeater defects that deviate from an expected group attribute distribution are classified at 106 as nuisance.

Optionally, repeater defects can be confirmed after step 103 or step 106 using an SEM. Once confirmed as a repeater defect, the repeater defect can then be compared with already existing database maintained for these repeaters, resulting in accurate identification of adders, which may be particles which landed (e.g., got added) on the photomask and then printed on the wafer. The database can then be updated to include new adders.

Some or all of the steps of method 100 can be performed using a processor.

Steps 105 and 106 may be performed independent of the rest of the steps of FIG. 1. For example, other defect inputs can be used for the steps 105 and 106 besides repeater defects. The repeater defects also can be obtained with different techniques than the embodiments that are illustrated.

A micro care area database can be established to monitor addition of new reticle defects. This database can include data from a BBP tool for both step 101 and step 103 in FIG. 1. With the database being maintained for reticle repeaters, embodiments of the method disclosed herein can be used to accurately identify new adders on the reticle and can be used to qualify EUV mask cleaning tools by performing high sensitive inspections primarily with or only with database based micro care areas.

The database can be used to review confirmation of repeater defects across multiple wafers. This can help identify adders. Entries in the database can be compared to existing micro care areas from previous wafers. The database can be updated with new repeater defect locations.

A reticle or photomask cleaning process can be monitored based on the micro care areas from the database. The database can be updated based on the results of this cleaning process. For example, there may be structures on a photomask that are difficult to print. Micro care areas can be created around all the locations of these structures. This can be referred to as a care area database. Those care areas can then be used to inspect areas with higher sensitivity or other critical areas.

A reticle stack can be used to identify repeater candidates. After reducing the number of known defects by cleaning the mask, an updated care area database can be generated.

With a small micro care area size and limited number of micro care areas, the inspection can be done with high sensitivity. For example, micro care are size can be around 5×5 pixels and the total number of micro care areas by die can range from a few to several million. Use of micro care areas can counter the disadvantages of robust average algorithms where a user has limited ability to distinguish printability variations of repeaters.

Figure 2:
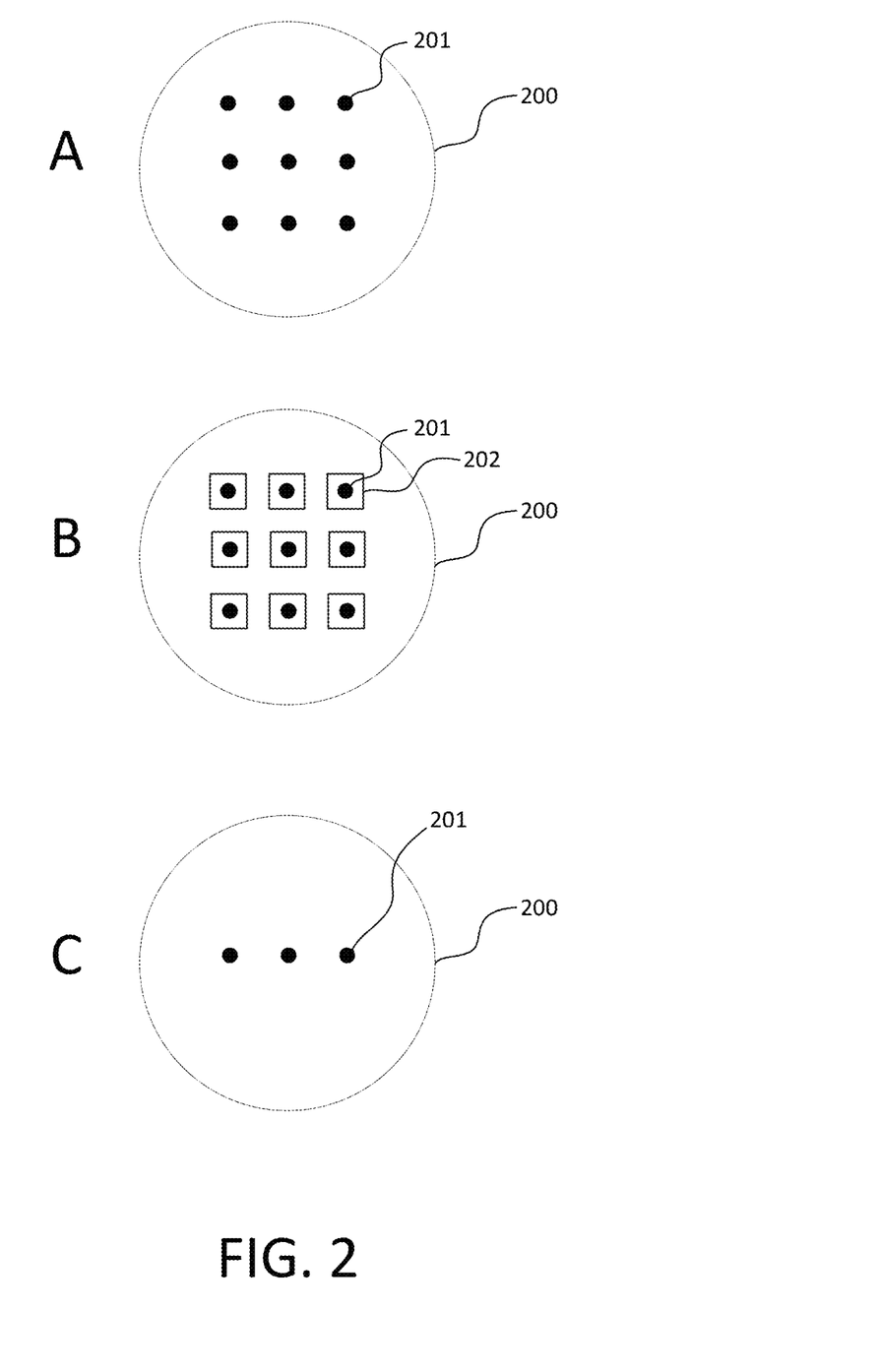
FIG. 2 is an example of the embodiment of FIG. 1.

FIG. 2 is an example of the embodiment of FIG. 1. Locations of the repeater defects 201 on the wafer 200 are determined in A. Micro care areas 202 are formed around locations of the repeater defects 201 in B. In C, nuisance are removed, which leaves only the repeater defects 201.

As seen in steps 105 and 106 of FIG. 1, attributes that describe an entire group of repeater defects can be calculated. If other detected repeater defects deviate from the expected group attribute distribution (i.e., are inconsistent) then these repeater defects can be considered as nuisance. This can enable the scan to run hotter.

Attributes can be calculated to describe an entire group of repeater defects. If other repeater defects deviate from the expected group distribution (e.g., are inconsistent), then the repeater defects can be considered as nuisance. The threshold can be used to detect deviance. For example, if at least 95% of the detected repeater defects are dark on a bright background it may be a real repeater.

The group attribute distribution can be based one or more of: all identified repeater defects on the wafer; all repeater defects of a same defect type; all repeater defects with a same design structure on the wafer; all repeater defects with a same die coordinate; all repeater defects with a same reticle coordinate; all repeater defects with a same background structure; or all repeater defects with a same wafer-to-wafer coordinate across multiple wafers. Other attributes are possible.

The attributes of the repeater defects within a group can be compared based on defect properties. These attributes can include a difference in gray level of the defect (polarity), the shape or contour of a point spread function, the size of a defect, brightness, or feature vectors. Other attributes are possible.

The exact defect location can be determined using design based alignment.

Locations on the wafer to skip during a subsequent inspection due to presence of the nuisance can be generated. For example, a particular nuisance area or areas can be designated.

Newly calculated attributes can be derived from machine learning experiments. Machine learning algorithms can be used to find outliers in certain defect groups. In an instance, unsupervised learning algorithms can be used to find defect outliers in an N dimensional attribute space. For example, a Gaussian can be fitted to a cluster of defects with certain attributes and detect outliers (e.g., as anomaly detection). In another instance, convolutional neural networks can use images as input dataset and calculate a new attribute, which may be the values of the logit function. If there is a wide distribution of logit values within a group of defects, then it is more likely a nuisance.

Figure 3:
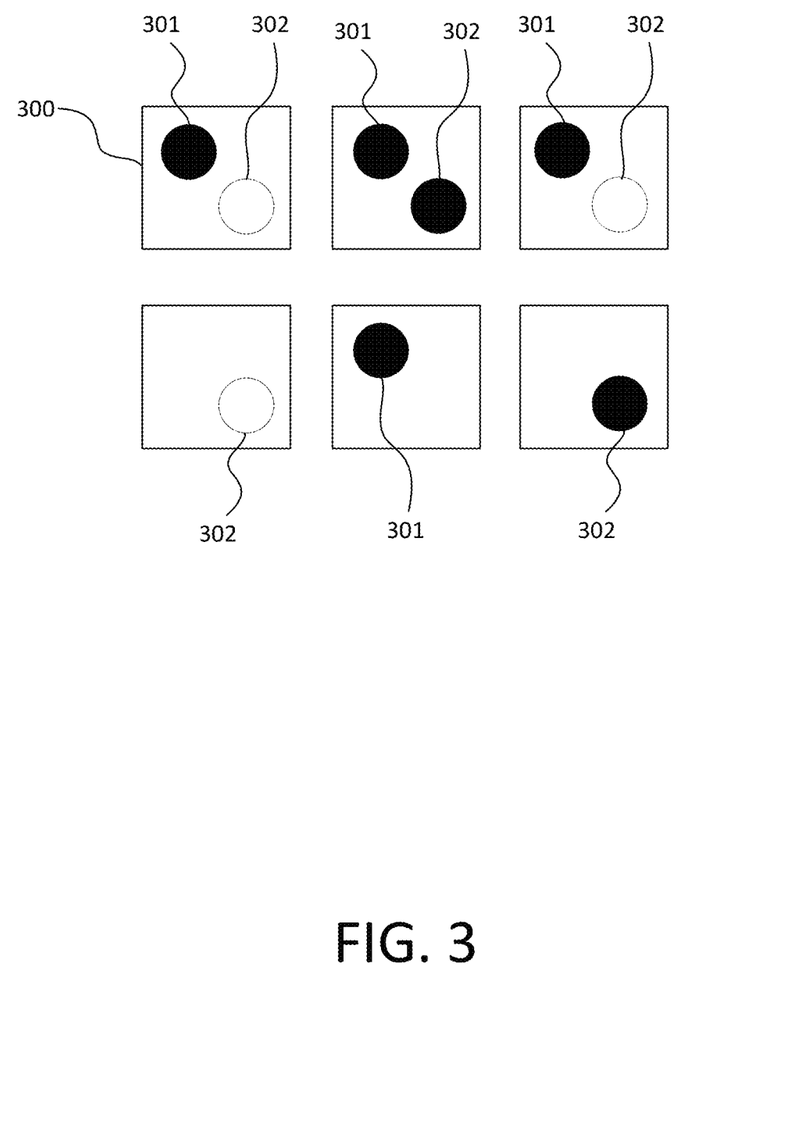
FIG. 3 is another example of the embodiment of FIG. 1.

FIG. 3 is another example of the embodiment of FIG. 1. In this example, assume there are repeater defects of the same type occurring in at least one of the two locations within every die 300. All first type repeater defects 301 form a group and all second type repeater defects 302 form another group. All first type repeater defects 301 show up as dark in a difference image. Second type repeater defects 302 sometimes show up as dark in the difference image and sometimes as bright, which indicates a change in defect polarity. Consequently, first type repeater defects 301 are DOI. Second type repeater defects 302 are nuisance because there is an inconsistency in an attribute within the group, namely polarity.

While the embodiment of FIGS. 1-3 are disclosed with respect to repeater defects, the embodiments disclosed herein can be applied to other types of defects.

Figure 4:
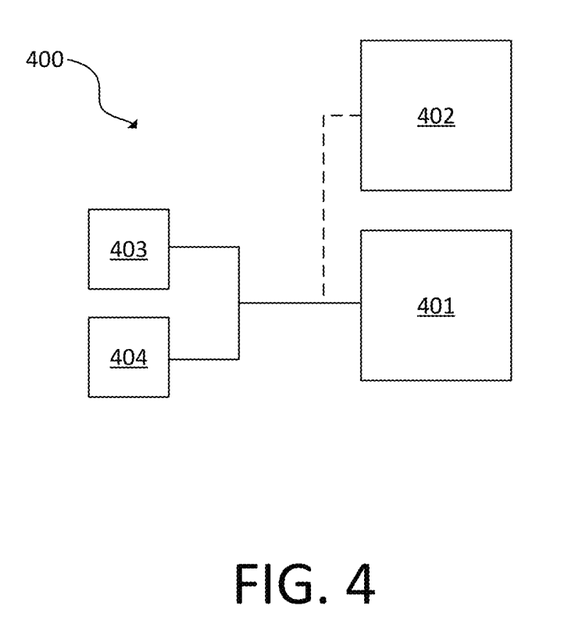
FIG. 4 is a block diagram of a system in accordance with the present disclosure

FIG. 4 is a system drawing of a system 400. The system 400 includes a wafer inspection tool 401 and optional wafer inspection tool 402. The wafer inspection tool 401 and wafer inspection tool 402 may be a BBP tool or an SEM. The wafer inspection tool also may be a laser scanning tool, an electron beam inspector, or other inspection systems. A BBP tool can be configured to perform a hot scan to capture inspection results.

A processor 403 and an electronic data storage unit 404 in electronic communication with the processor 403 are in electronic communication with the wafer inspection tool 401 and the wafer inspection tool 402. The processor 403 may include a microcontroller, a microprocessor, or another device.

The processor 403 and electronic data storage unit 404 may be part of the wafer inspection tool 401 or another device. In an example, the processor 403 and electronic data storage unit 404 may be a standalone control unit or in a centralized quality control unit. Multiple processors 403 and electronic data storage units 404 may be used.

The processor 403 may be implemented in practice by any combination of hardware, software, and firmware. Also, its functions as described herein may be performed by one unit, or divided up among different components, each of which may be implemented in turn by any combination of hardware, software and firmware. Program code or instructions for the processor 403 to implement various methods and functions may be stored in readable storage media, such as a memory in the electronic data storage unit 404 or other memory.

The processor 403 may be coupled to the components of the system 400 in any suitable manner (e.g., via one or more transmission media, which may include wired and/or wireless transmission media) such that the processor 403 can receive the output generated by the system 400. The processor 403 may be configured to perform a number of functions using the output.

The processor 403, other system(s), or other subsystem(s) described herein may be part of various systems, including a personal computer system, image computer, mainframe computer system, workstation, network appliance, internet appliance, or other device. The subsystem(s) or system(s) may also include any suitable processor known in the art, such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

An additional embodiment relates to a non-transitory computer-readable medium storing program instructions executable on a processor for performing a computer-implemented defect detection or wafer inspection, as disclosed herein. In particular, the processor 403 can be coupled to a memory in the electronic data storage unit 404 or other electronic data storage medium with non-transitory computer-readable medium that includes program instructions executable on the processor 403. The computer-implemented method may include any step(s) of any method(s) described herein. For example, the processor 403 may be programmed to perform some or all of the steps of FIG. 1 or FIGS. 5-7, or other embodiments disclosed herein. The memory in the electronic data storage unit 404 or other electronic data storage medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

The micro care area database can be stored on the electronic data storage unit 404 or on other storage media.

In an embodiment, soft repeaters can be identified and nuisance in repeater defect images can be reduced. Repeater defects can include both hard repeaters (which are always visible on a die) and soft repeaters (which may not always be visible on a die). If only a limited number of dies are imaged, it can be challenging to detect repeater defects and can be especially challenging to detect soft repeaters.

For example, since soft repeaters might not be visible or even printed in every die, it may be important to run hotter at locations where soft repeaters are expected by creating micro care areas. In addition, consistency-based attributes can be used to find out if there are outliers within a group which makes the defect unlikely to be a DOI.

In an instance, a first wafer can be inspected and/or recorded at t=0 to detect and/or record systematic nuisance on a reticle. This can be part of an integrated solution for EUV mask inspection. At t>0 (e.g., three weeks later), a second wafer can be inspected and/or recorded. Systematic nuisance in t>0 can be subtracted from t=0. Random reticle defects can be reported. This can provide a lower nuisance rate and, thus, higher sensitivity to DOI. For example, t=0 can be when the reticle is clean and/or problem-free and t>0 can mean that there are particles on and/or other problems with the reticle. These other problems may be caused by misalignment during printing or reticle defects.

Figure 5:
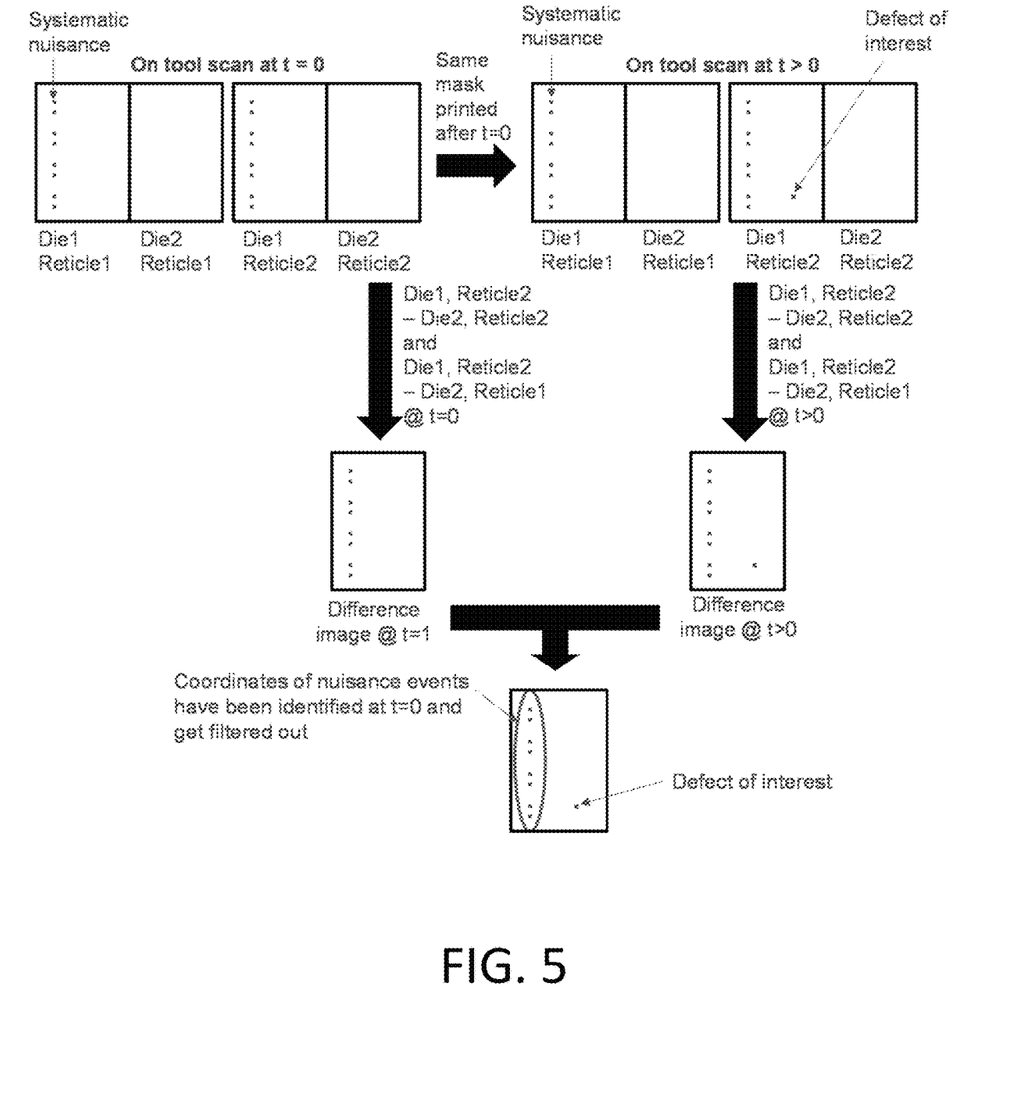
FIG. 5 is a first embodiment of nuisance reduction in accordance with the present disclosure.

FIG. 5 is a first embodiment of nuisance reduction. A first die and a second die are each imaged using a reticle at two different positions (reticle1, reticle2) on a first wafer (t=0) and two different positions (reticle1, reticle2) on a second wafer (t>0). The two different positions may be, for example, different rows on the wafer. The first die and the second die may be neighboring dies or may have other spatial relationships. The image processing steps may be performed by a processor.

A first wafer difference image is calculated. To do so, a difference image of the first die and the second die at a second position on the first wafer is calculated. A difference image of the first die at the second position on the first wafer and the second die at a first position on the first wafer also is calculated. Then the first wafer difference image is calculated from the two resulting difference images.

A second wafer difference image is calculated. To do so, a difference image of the first die and the second die at a second position on the second wafer is calculated. A difference image of the first die at the second position on the first wafer and the second die at a first position on the second wafer also is calculated. Then the second wafer difference image is calculated from the two resulting difference images.

Systematic defects in the first difference image can be found using coordinate-based defect source analysis. The systematic defects in the first wafer difference image can be subtracted from the second wafer difference image based on their coordinates. Existence of a DOI in the second wafer difference image can be determined after the common (e.g., systematic) defects have been excluded.

Figure 6:
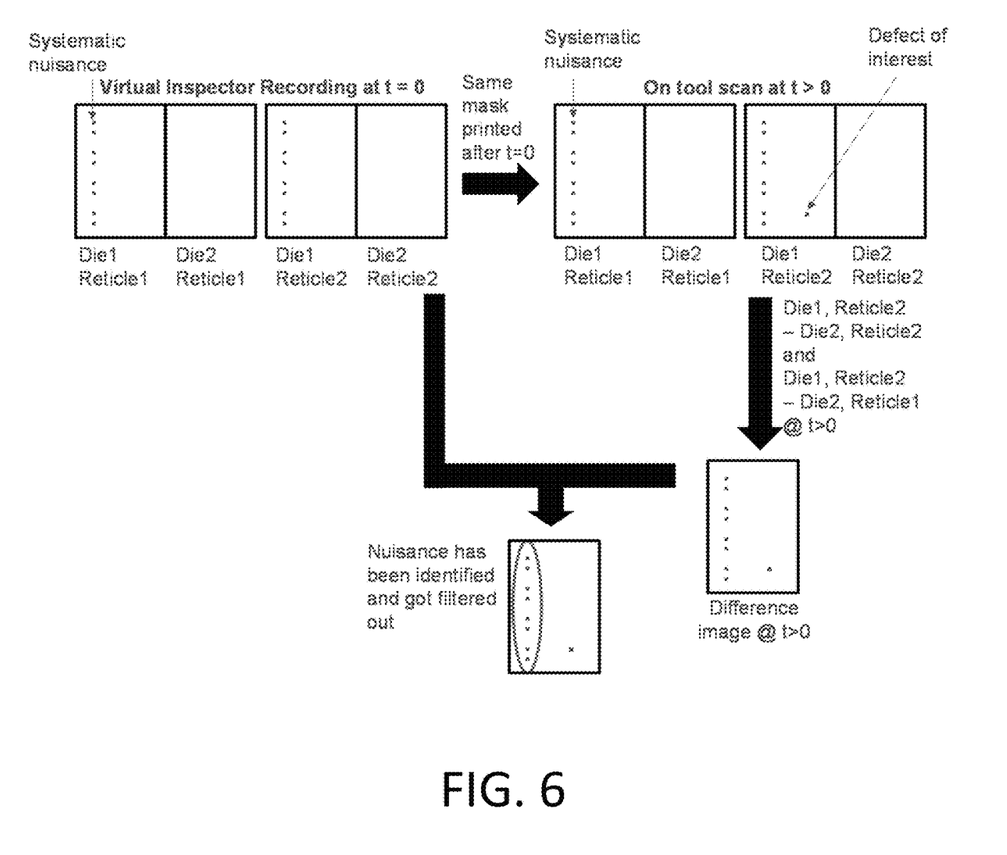
FIG. 6 is a second embodiment of nuisance reduction in accordance with the present disclosure.

FIG. 6 is a second embodiment of nuisance reduction. A first die and a second die are each imaged using a reticle at two different positions (reticle1, reticle2) on a first wafer (t=0) and two different positions (reticle1, reticle2) on a second wafer (t>0). The two different positions may be, for example, different rows on the wafer. The first die and the second die may be neighboring dies or may have other spatial relationships. The image processing steps may be performed by a processor.

A difference image of the first die and the second die at a second position on the second wafer is calculated. A difference image of the first die at the second position on the first wafer and the second die at a first position on the second wafer is calculated. Then a wafer difference image is calculated from the two resulting difference images.

Existence of a defect of interest in the wafer difference image is determined. Images can be retrieved from the storage medium. The images are at the same location on the first wafer (e.g., t=0) as the first die and the second die on the second wafer that were used in the calculating. Presence of the defect of interest can be evaluated in the images from the storage medium. Nuisance can be filtered from the wafer difference image.

Figure 7:
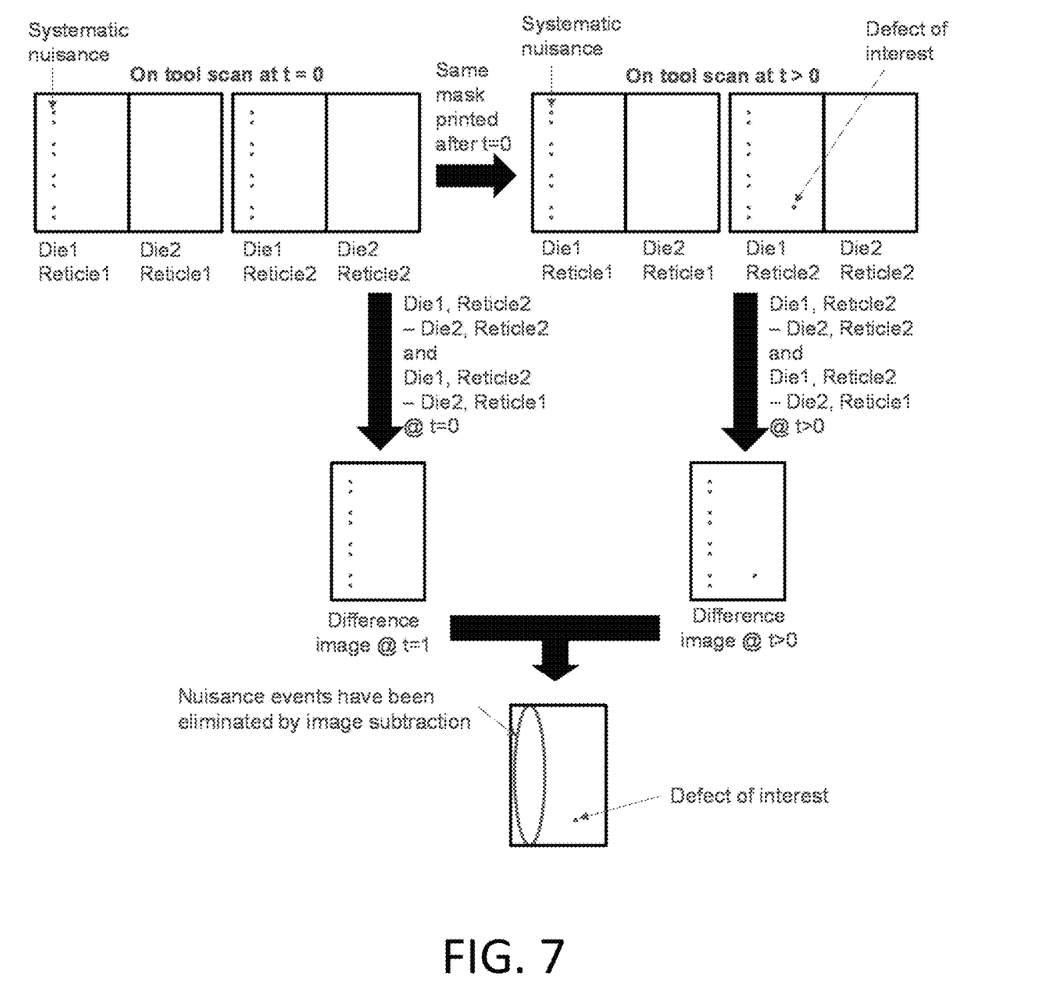
FIG. 7 is a third embodiment of nuisance reduction in accordance with the present disclosure

FIG. 7 is a third embodiment of nuisance reduction. A first die and a second die are each imaged using a reticle at two different positions (reticle1, reticle2) on a first wafer (t=0) and two different positions (reticle1, reticle2) on a second wafer (t>0). The two different positions may be, for example, different rows on the wafer. The first die and the second die may be neighboring dies or may have other spatial relationships. The image processing steps may be performed by a processor.

A first wafer difference image is calculated. To do so, a difference image of the first die and the second die at a second position on the first wafer is calculated. A difference image of the first die at the second position on the first wafer and the second die at a first position on the first wafer also is calculated. Then the first wafer difference image is calculated from the two resulting difference images.

A second wafer difference image is calculated. To do so, a difference image of the first die and the second die at a second position on the second wafer is calculated. A difference image of the first die at the second position on the first wafer and the second die at a first position on the second wafer also is calculated. Then the second wafer difference image is calculated from the two resulting difference images.

The second wafer difference image is subtracted from the first wafer difference image. Existence of a defect of interest in the second wafer difference image can be determined after the subtracting.

The embodiments of FIGS. 5-7 can be used with micro care areas as do not inspect care areas. Thus, inspection may run cold instead of hot within these micro care areas. For example, if it is determined that there are certain structures on the wafer which will show up as defects that a semiconductor manufacturer wants to ignore, do not inspect care areas can be created around them so that these structures can be ignored during inspection. These structures can be found during a scan at t=0 or the semiconductor manufacturer may provide a database of where the structures are located based on other inspection results (e.g., using an electron beam). Such structures to be ignored may be noisy.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits may be formed on a wafer, and the term wafer as used herein is intended to encompass a wafer on which any type of device known in the art is being fabricated.

Although embodiments are described herein with respect to wafers, it is to be understood that the embodiments may be used for another specimen such as a reticle, which may also be commonly referred to as a mask or a photomask. Many different types of reticles are known in the art, and the terms "reticle," "mask," and "photomask" as used herein are intended to encompass all types of reticles known in the art.

Each of the steps of the method may be performed as described herein. The methods also may include any other step(s) that can be performed by the processor and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A method comprising:
   determining locations, using a processor, of repeater defects on a wafer;
   creating, using the processor, a micro care area around each of the locations, wherein the micro care area is from one pixel square to ten by ten pixels square;
   inspecting the micro care areas on the wafer using a wafer inspection tool;
   identifying additional repeater defects in the micro care areas;
   comparing, using the processor, at least one attribute of the repeater defects and the additional repeater defects, wherein the attribute includes polarity and the polarity is a difference in gray level between defects; and
   classifying, using the processor, any of the repeater defects and the additional repeater defects with the attribute that deviates from an expected group attribute distribution as nuisance.

2. The method of claim 1, wherein the group attribute distribution is based one or more of:
   all identified repeater defects on the wafer;
   all repeater defects of a same defect type;
   all repeater defects with a same design structure on the wafer;
   all repeater defects with a same die coordinate;
   all repeater defects with a same reticle coordinate;
   all repeater defects with a same background structure; or
   all repeater defects with a same wafer-to-wafer coordinate across multiple wafers.

3. The method of claim 1, wherein the attribute further includes at least one of shape of a point spread function, contour of a point spread function, size, brightness, or feature vectors.

4. The method of claim 1, wherein the determining is for an entirety of a surface of the wafer.

5. The method of claim 1, wherein the determining is for only a die row on the wafer.

6. The method of claim 1, further comprising generating, using the processor, locations on the wafer to skip during a subsequent inspection due to presence of the nuisance.

7. The method of claim 1, wherein determining the locations includes using repeater in array or standard reference die for logic areas.

8. The method of claim 1, wherein determining the locations includes a die-to-die inspection.

9. A system comprising:
   a processor and an electronic data storage unit in electronic communication with the processor, wherein the processor is in electronic communication with a wafer inspection tool, and wherein the processor is configured to execute instructions that:
   determine locations of repeater defects on a wafer;
   create a micro care area around each of the locations, wherein the micro care area is from one pixel square to ten by ten pixels square;
   identify additional repeater defects in the micro care areas based on an additional inspection of the micro care areas;
   compare at least one attribute of the repeater defects and the additional repeater defects wherein the attribute includes polarity and the polarity is a difference in gray level between defects; and
   classify any of the repeater defects and the additional repeater defects with the attribute that deviates from an expected group attribute distribution as nuisance.

10. The system of claim 9, wherein the group attribute distribution is based on one or more of:
    all identified repeater defects on the wafer;
    all repeater defects of a same defect type;
    all repeater defects with a same design structure on the wafer;
    all repeater defects with a same die coordinate;
    all repeater defects with a same reticle coordinate;
    all repeater defects with a same background structure; or
    all repeater defects with a same wafer-to-wafer coordinate across multiple wafers.

11. The system of claim 9, wherein the attribute further includes at least one of shape of a point spread function, contour of a point spread function, size, brightness, or feature vectors.

12. The system of claim 9, wherein the processor is further configured to execute instructions that generate locations on the wafer to skip during a subsequent inspection due to presence of the nuisance.

13. The system of claim 9, wherein the processor is part of the wafer inspection tool.

14. A method comprising:
    receiving, at a processor, a plurality of repeater defects;
    comparing, using the processor, at least one attribute of the repeater defects, wherein the attribute includes at least polarity of the repeater defects and wherein the polarity is a difference in gray level between repeater defects; and separating, using the processor, any of the repeater defects with the attribute that deviates from an expected group attribute distribution as nuisance.

15. The method of claim 14, wherein the group attribute distribution is based on one or more of:
all identified repeater defects on the wafer;
all repeater defects of a same defect type;
all repeater defects with a same design structure on the wafer;
all repeater defects with a same die coordinate;
all repeater defects with a same reticle coordinate;
all repeater defects with a same background structure; or
all repeater defects with a same wafer-to-wafer coordinate across multiple wafers.

16. The method of claim 14, wherein the attribute further includes at least one of shape of a point spread function, contour of a point spread function, size, brightness, or feature vectors.

17. The method of claim 14, further comprising generating, using the processor, locations on a wafer to skip during a subsequent inspection due to presence of the nuisance.

* * * * *